(12) United States Patent
Hanson

(10) Patent No.: US 10,349,177 B2
(45) Date of Patent: Jul. 9, 2019

(54) WIRELESS STEREO SLEEP MASK

(71) Applicant: Cherie Hanson, Ogden, UT (US)

(72) Inventor: Cherie Hanson, Ogden, UT (US)

( * ) Notice: Subject to any disclaimer, the term of this patent is extended or adjusted under 35 U.S.C. 154(b) by 0 days.

(21) Appl. No.: 16/046,826

(22) Filed: Jul. 26, 2018

(65) Prior Publication Data

US 2019/0037314 A1    Jan. 31, 2019

Related U.S. Application Data

(60) Provisional application No. 62/537,222, filed on Jul. 26, 2017.

(51) Int. Cl.
| | |
|---|---|
| *A61F 9/04* | (2006.01) |
| *A61M 21/02* | (2006.01) |
| *H04R 5/04* | (2006.01) |
| *H04R 5/033* | (2006.01) |
| *G06F 3/16* | (2006.01) |
| *H04S 1/00* | (2006.01) |
| *A61M 21/00* | (2006.01) |

(52) U.S. Cl.
CPC .............. *H04R 5/033* (2013.01); *A61F 9/04* (2013.01); *A61M 21/02* (2013.01); *G06F 3/165* (2013.01); *H04R 5/04* (2013.01); *H04S 1/007* (2013.01); *A61M 2021/0027* (2013.01); *A61M 2205/3561* (2013.01); *A61M 2205/80* (2013.01); *A61M 2205/8206* (2013.01); *A61M 2209/088* (2013.01); *H04R 2420/07* (2013.01); *H04R 2420/09* (2013.01)

(58) Field of Classification Search
CPC ......... A61F 9/04; H04R 2420/07; H04R 5/02; H04R 1/026; H04R 1/1091; A61M 21/02
USPC ............................. 381/300, 311; 340/539.11
See application file for complete search history.

(56) References Cited

U.S. PATENT DOCUMENTS

| | | | | |
|---|---|---|---|---|
| 2014/0009282 A1* | 1/2014 | Baloa Welzien | ...... | G04G 11/00 340/539.11 |
| 2017/0264994 A1* | 9/2017 | Gordon | ................ | H04R 1/1091 |

* cited by examiner

*Primary Examiner* — Thjuan K Addy

(57) ABSTRACT

A wireless stereo sleep mask is an apparatus that is used to block light from entering a user's eyes, while simultaneously providing the user a way to wirelessly interact with a smartphone or other similar devices. The apparatus includes an eye cover, an elastic strap, a first speaker, a second speaker, a control unit, and a wireless transceiver. The eye cover prevents light from disturbing the user. The first speaker and the second speaker are positioned in proximity to the user's ears. The control unit allows the user to adjust the volume of the first speaker and the second speaker. The elastic strap ensures the user is comfortable while wearing the eye cover. A microphone integrated into the control unit provides the user the ability to speak during phone calls, and to control the present invention using voice commands.

8 Claims, 5 Drawing Sheets

WIRELESS STEREO SLEEP MASK

The current application claims a priority to the U.S. Provisional Patent application Ser. No. 62/537,222 filed on Jul. 26, 2017.

FIELD OF THE INVENTION

The present invention generally relates to a sleeping device. More specifically, the wireless stereo sleep mask relates to an eye cover that prevents light from disturbing an individual's view. The present invention further includes a pair of speakers with corresponding controls that allow users to wirelessly pair their devices to the speakers for accessing personal music libraries.

BACKGROUND OF THE INVENTION

With the current abundance of musical content, headphones have become omnipresent. Full headphones and ear buds alike are connected to mobile devices in order to provide the user with music and audio capabilities as desired. The multitude of listening options means that a user has a seemingly endless supply of listening means. Headphones tend to be most effective when listening at home or in private locations, while ear buds are excellent for listening while on the go. Similarly, many of these devices are equipped with microphones, thereby allowing users to make calls without holding their phones to their ears.

However, such devices have several drawbacks that make them ineffective for many applications, especially in sleeping. With such prior devices, the speaker is bulky or protrudes into the ear causing discomfort if laid upon when in a resting position on a pillow or on a person's side. Some often require auxiliary cords to plug into external devices such as cell phones or other devices that can cause the wearer to become entangled during sleep. Heretofore, there has not been an adequate solution to allow a user to wear comfortable private audio devices while simultaneously providing an improved eye mask for keeping ambient light out of a user's eyes. What is needed is a device that allows the user to hold speakers in an adjustable position over ears and listen to audio while simultaneously providing a comfortable eye mask for keeping ambient light out of a user's eyes. Such a needed device would be adaptable to a variety of head shapes without bulky fasteners that could cause discomfort or cause hair to become entangled and would also allow for removal of the hardware to wash the eye mask and band. Further desirable is such a device with a microphone that allows the user to connect wirelessly with a smartphone device, thus enabling the user to conduct phone calls without removing the eye cover.

The wireless stereo sleep mask accomplishes these objectives. The present invention has a face mask that covers the user's eyes, allowing the user to go to sleep easily in spite of the brightness of the surrounding area. A speaker is positioned against each of the user's ears, allowing the user to clearly hear music and sounds. A wireless transceiver allows the user to electronically pair devices, including smartphones and other wireless music players, to the present invention. An elastic band enables comfortable addition of the present invention to the user's head, so the connection means does not disturb the user's ability to fall asleep. Furthermore, the controls include a microphone, so the user can speak during phone calls, as well as a set of volume controls that allow for adjustment of speaker volume.

DETAILED DESCRIPTION OF THE INVENTION

All illustrations of the drawings are for the purpose of describing selected versions of the present invention and are not intended to limit the scope of the present invention.

Figure 1:
FIG. 1 is a front-top perspective view of the present invention.

The present invention is a wireless stereo sleep mask that prevents light from entering the user's eyes during sleep or restful time. The present invention uses a pair of speakers connected to a control module that allows the user to play music and take phone calls without removing the present invention. The present invention comprises an eye cover 1, an elastic strap 6, a first speaker 14, a second speaker 15, a control unit 16, and a wireless transceiver 23. The eye cover 1 is a comfortable, lightproof mask, as seen in FIG. 1, that eliminates visual stimuli from disturbing the user. The elastic strap 6 is a flexible connector that joins opposing ends of the eye cover 1. The first speaker 14 and the second speaker 15 are electrical components which respond to signals from the control unit 16 by producing sound waves. The control unit 16 is a series of electrical connections that enables the user to interact with the first speaker 14 and the second speaker 15. The wireless transceiver 23 enables the user to interact with audio content from a connected device. The wireless transceiver 23, in conjunction with the control unit 16, allows the user to electronically pair to devices and adjust volume while taking calls or listening to music.

Figure 2:
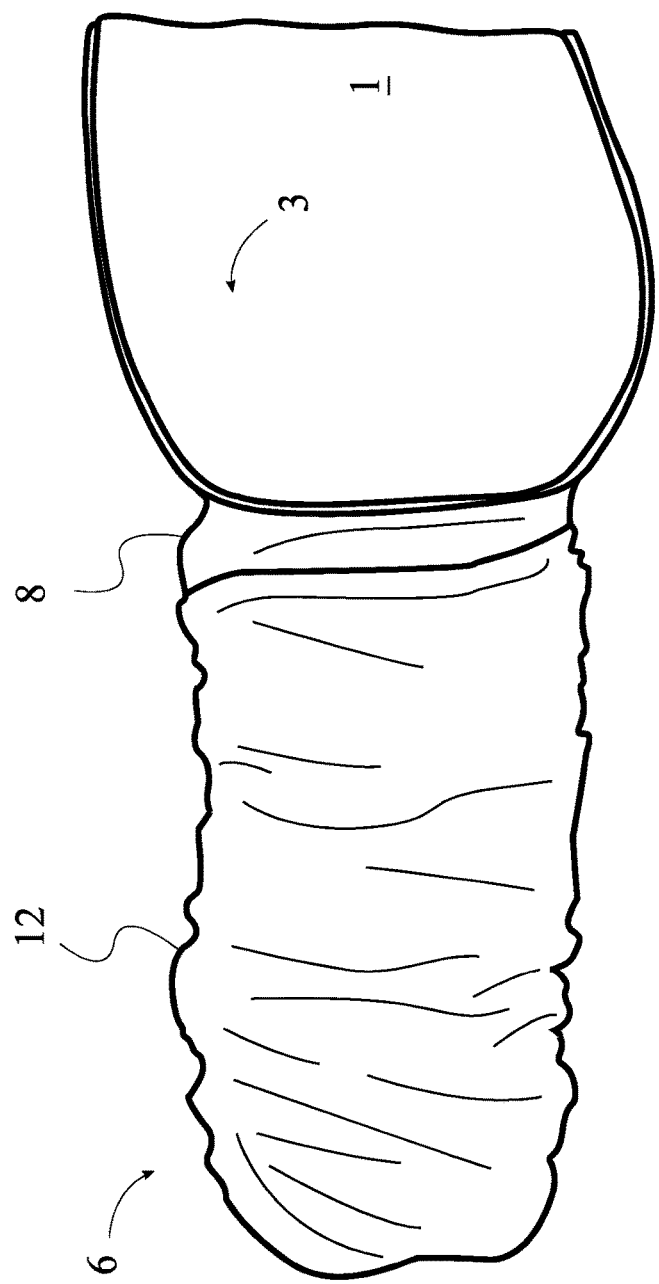
FIG. 2 is a left perspective view of the present invention.

The general configuration of the aforementioned components allows the present invention to efficiently and effectively provide the user with a means of blocking light from the user's eyes and connecting to the user's phone or devices to access music and sound/speech functions for phone calls. The eye cover 1 comprises a first temple-bracing portion 2 and a second temple-bracing portion 3. The first temple-bracing portion 2 and second temple-bracing portion 3 are segments of the eye cover 1 which contact different parts of the user's face. The first temple-bracing portion 2 and the second temple-bracing portion 3 are positioned opposite to each other across the eye cover 1. This arrangement allows for subsequent relative positioning of the first speaker 14, the second speaker 15, and the elastic strap 6. The first temple-bracing portion 2 is terminally mounted to the elastic strap 6. In this way, the first temple-bracing portion 2 is located proximally to the elastic strap 6. Similarly, the second temple-bracing portion 3 is terminally mounted to the elastic strap 6, opposite the first temple-bracing portion 2, as seen in FIG. 2. In this way, the second temple-bracing portion 3 is located proximally to the elastic strap 6, so that the first temple-bracing portion 2 and the second temple-bracing portion 3 are on opposite ends of the elastic strap 6. The first speaker 14 and the second speaker 15 are housed within the elastic strap 6. In this way, the first speaker 14 and the second speaker 15 remain in place during use. The first speaker 14 is positioned adjacent to the first temple-bracing portion 2. This arrangement ensures that the first speaker 14 is located proximally to the user's ear. Similarly, the second speaker 15 is positioned adjacent to the second temple-bracing portion 3. This arrangement ensures that the second speaker 15 is located proximally to the user's other ear, opposite the first speaker 14. The wireless transceiver 23 is electronically connected to the control unit 16. This allows the control unit 16 to send and respond to signals sent by the wireless transceiver 23. The control unit 16 is electrically connected to the first speaker 14 and the second speaker 15. This arrangement enables the control unit 16 to send signals to the first speaker 14 and the second speaker 15.

The eye cover 1 and the elastic strap 6 together provide comfortable compression that keeps the present invention in place on a user's head. The eye cover 1 comprises a velvety enclosure 4 and a padding 5. The velvety enclosure 4 is a soft, smooth material which contacts the user's face, ensuring comfort in wearing and using the present invention. The padding 5 is a flexible foam, stuffing, high loft batting, or other such material that increases the comfort of the user while the user wears the present invention. The padding 5 is positioned within the velvety enclosure 4. This arrangement ensures optimal user comfort, as well as providing a semi-rigid structure to assist the user in properly arranging the present invention on the user's face. The padding 5 is distributed throughout the velvety enclosure 4. In this way, the padding 5 provides comfort across the contacting area of the eye mask.

Figure 4:
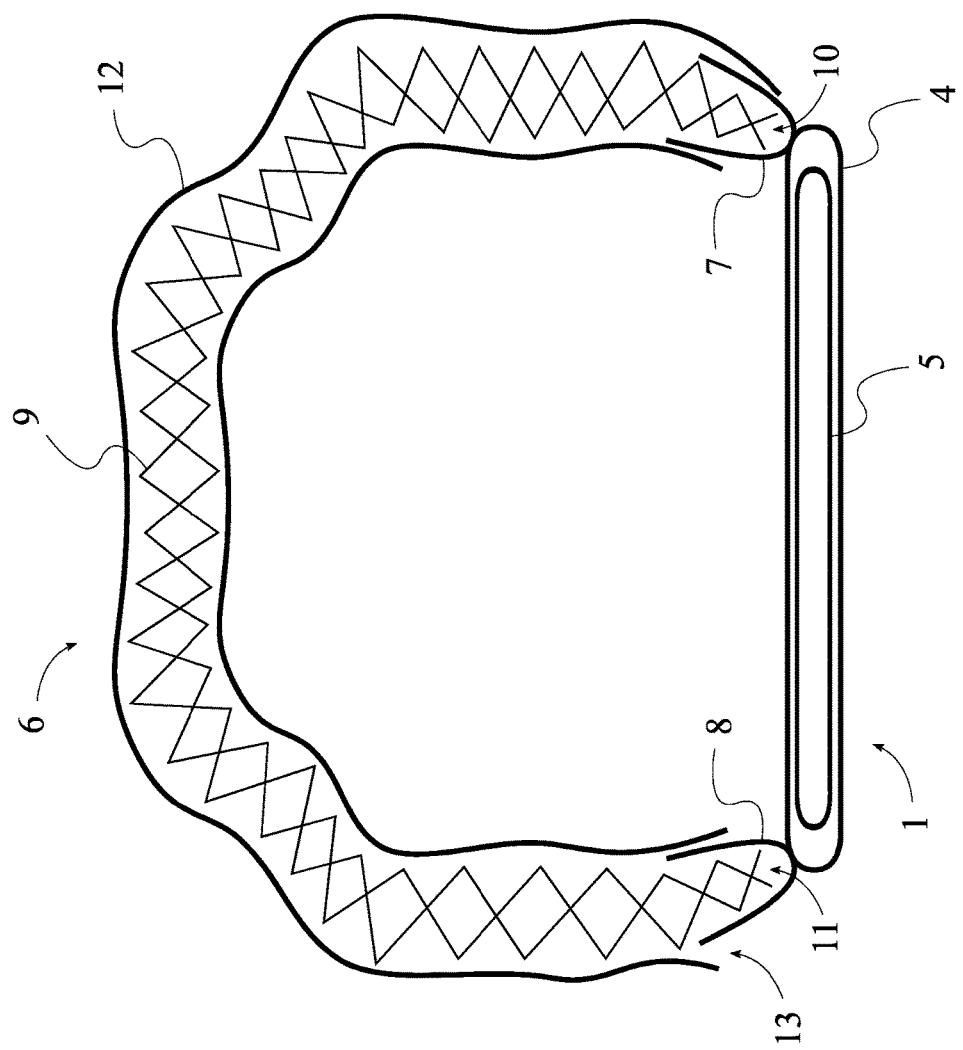
FIG. 4 is a top schematic view of the present invention.

In order to secure the present invention in place against the user's head and face and to secure the first speaker 14 and the second speaker 15 in place, the present invention utilizes the elastic strap 6. The elastic strap 6 comprises a first pocket 7, a second pocket 8, and an elastic mesh band 9. The first pocket 7 and the second pocket 8 are openings into the elastic strap 6. The elastic mesh band 9 is a flexible, stretchy connector that provides the compression that secures the present invention in place during use, as seen in FIG. 4. The elastic mesh band 9 comprises a first band end 10 and a second band end 11. The first band end 10 is the segment of the elastic mesh band 9, opposite the second band end 11. The first pocket 7 is connected adjacent to the first temple-bracing portion 2. Similarly, the second pocket 8 is connected adjacent to the second temple-bracing portion 3. This arrangement ensures the first pocket 7 is on the side of the eye cover 1, opposite the second pocket 8, and that both the first pocket 7 and the second pocket 8 are positioned proximally to the user's ears. The first band end 10 is connected within the first pocket 7. This positions the elastic mesh band 9 appropriately relative to the eye cover 1. The second band end 11 is connected within the second pocket 8. This positions the elastic mesh band 9 appropriately relative to the eye cover 1.

Figure 3:
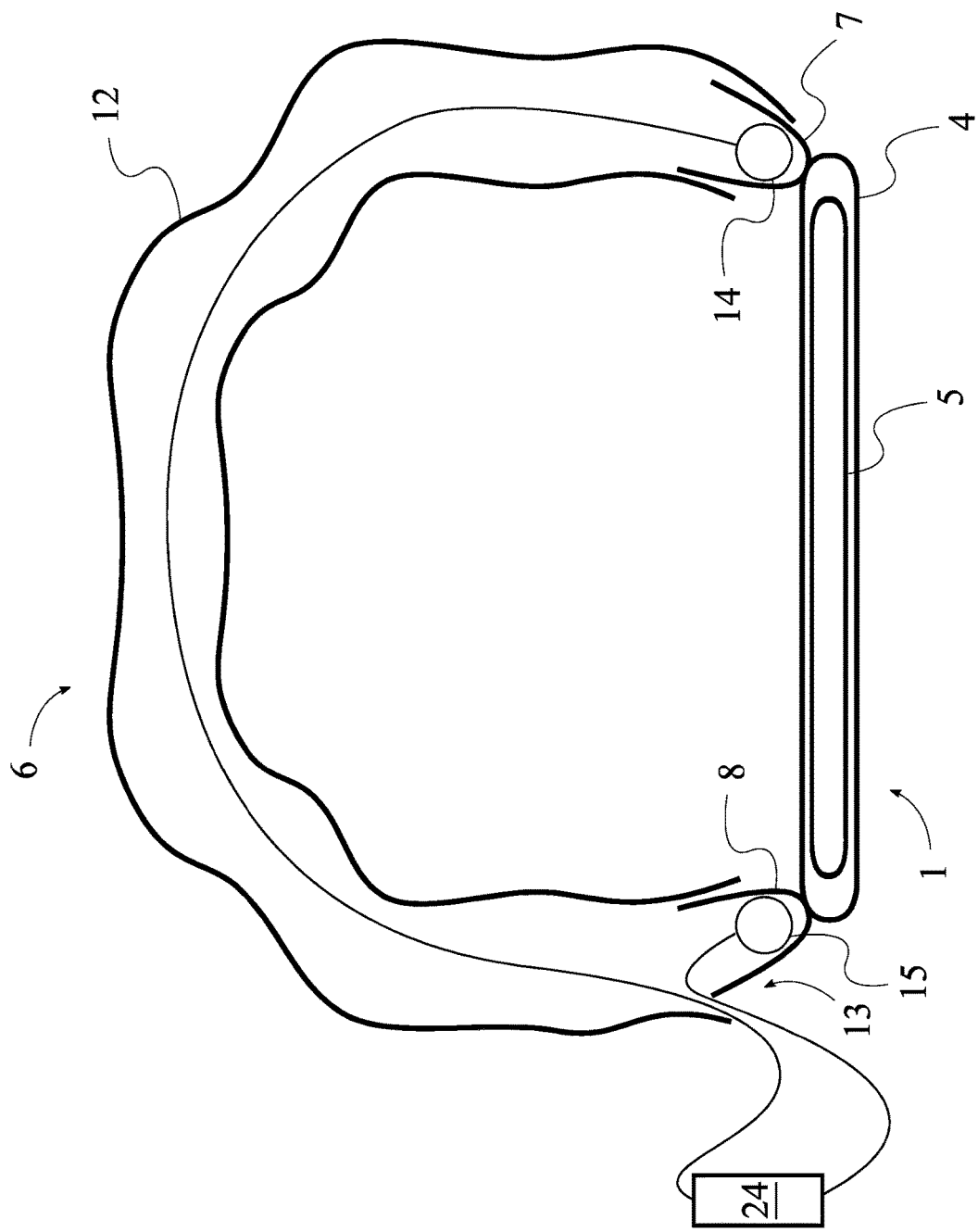
FIG. 3 is a top schematic view of the present invention.

The first pocket 7 and the second pocket 8 have space available for the first speaker 14 and the second speaker 15, as seen in FIG. 3. The first speaker 14 is situated within the first pocket 7. This arrangement ensures that the first speaker 14 is in position near a user's ear, allowing for easy sound transmission to the user's ear. The second speaker 15 is situated within the second pocket 8. This arrangement ensures that the second speaker 15 is in position near a user's ear, allowing for easy sound transmission to the user's ear opposite the first speaker 14. This arrangement of the first speaker 14 and the second speaker 15 allows for optimal sound distribution to the user's ears.

The elastic strap 6 is under constant tension and therefore benefits from some level of protection. The elastic strap 6 further comprises a sleeve 12. The sleeve 12 is a soft fabric unit that improves the cushioning of the present invention. The elastic mesh band 9 traverses through the sleeve 12. This arrangement ensures that the elastic mesh band 9 is protected from potentially damaging physical stimuli. The first pocket 7 is telescopically engaged into the sleeve 12. This allows the sleeve 12 to cover the first pocket 7 and protect the components within. The second pocket 8 is telescopically engaged into the sleeve 12, opposite the first pocket 7. This allows the sleeve 12 to cover the second pocket 8 and protect the components within. Combined, the arrangement of the sleeve 12 relative to the first pocket 7 and the second pocket 8 ensures that wires and other components attached to the first speaker 14 and the second speaker 15 are adequately protected during use. In an exemplary embodiment, the length of the sleeve 12 is greater than the length of the elastic mesh band 9. This arrangement allows the sleeve 12 to elongate with the expanding elastic of the elastic mesh band 9.

In order to allow for user interaction with the first speaker 14 and the second speaker 15, the present invention further comprises a casing 24. The casing 24 is a protective structural unit that prevents damage to several electrical components and allows for mounting and arrangement of various controls. The wireless transceiver 23 and the control unit 16 are housed within the casing 24. This ensures that the control unit 16 and the wireless transceiver 23 are protected and near each other. The first speaker 14 is tethered adjacent to the casing 24. This arrangement allows the first speaker 14 to receive signals from the control unit 16. The second speaker 15 is tethered adjacent to the casing 24, opposite the first speaker 14. This arrangement allows the second speaker 15 to receive signals from the control unit 16 and allows for the first speaker 14 and the second speaker 15 to emit sound into both of a user's ears. Furthermore, the elastic strap 6 comprises an access opening 13. The access opening 13 is a space which allows the user to store and subsequently access the casing 24. The access opening 13 is laterally positioned on the elastic strap 6. In this way, the access opening 13 is easily accessible to the user. The casing 24 is externally positioned to the elastic strap 6, adjacent to the access opening 13. This arrangement ensures that the user can always grasp the control unit 16 to make adjustments to the volume output of the first speaker 14 and the second speaker 15. Alternatively, the casing 24 is situated within the elastic strap 6. In this way, the casing 24 is stored while the user wears the present invention without making adjustments to the speaker outputs.

Figure 5:
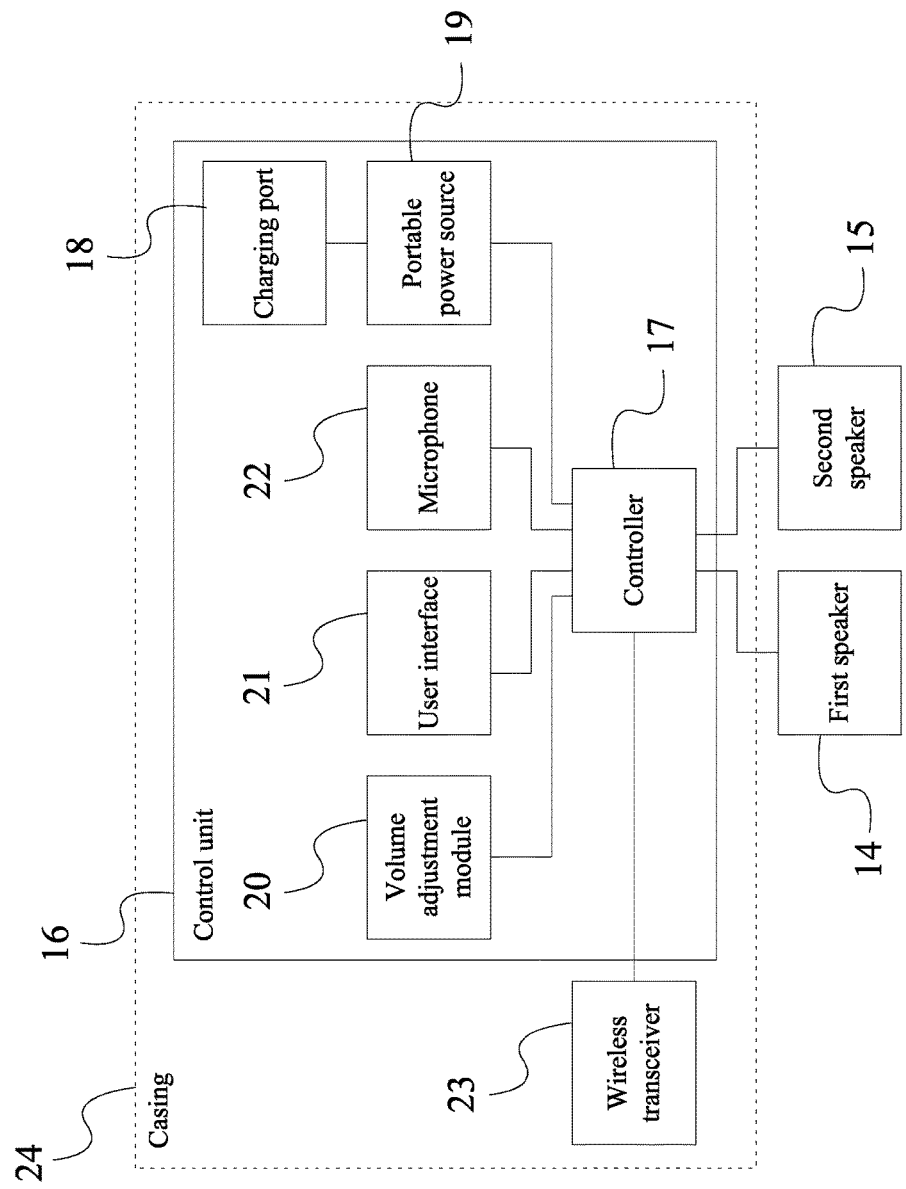
FIG. 5 is a process flow diagram depicting the control unit, first speaker, and second speaker of the present invention.

The control unit 16 is the interface between the user and the first speaker 14 and second speaker 15. The control unit 16 comprises a controller 17, a charging port 18, and a portable power source 19, as seen in FIG. 5. The controller 17 is the logic center of the control unit 16, providing the ability to accept electrical signal inputs, interpret those inputs, and consequently distribute electrical outputs throughout the present invention. The charging port 18 is an opening that allows for the input of a power plug, preferably a Universal Serial Bus (USB) 2.0 Micro-B 5-pin. The portable power source 19 is an electrical power storage unit that provides power to all electrical components as directed by the controller 17. The portable power source 19 is electrically connected to the charging port 18 and the controller 17. Connecting a power cord between the charging port 18 and an electrical outlet allows the battery to replenish electrical potential energy. The electrical connection between the portable power source 19 and the controller 17 allows the controller 17 to distribute the electrical power. The first speaker 14, the second speaker 15, and the wireless transceiver 23 are electronically connected to the controller 17. This arrangement allows the first speaker 14, the second speaker 15, and the wireless transceiver 23 to receive signals and power from and to the controller 17.

Some ancillary features of the control unit 16 improve the functionality of the present invention. Thus, the control unit 16 further comprises a volume adjustment module 20. The volume adjustment module 20 is a series of buttons, a wheel, a slider, or any of a variety of alternative input mechanisms that allow the user to adjust the intensity of sound output from the first speaker 14 and the second speaker 15. The volume adjustment module 20 is electronically connected to the controller 17. This allows changes in the volume adjustment module 20 to transmit signals directly to the controller 17 for subsequent signal interpretation. The control unit 16 further comprises a user interface 21. The user interface 21 is a button, series of buttons, switch, or other interaction mechanisms that allows the user to control the on/off state of the present invention, as well as to allow the wireless transceiver 23 to pair with the user's audio device. The user interface 21 is electronically connected to the controller 17. This arrangement allows changes in the user interface 21 to be received and subsequently interpreted by the controller 17. The control unit 16 further comprises a microphone 22. The microphone 22 is an audio capturing device that allows the user to utilize the present invention for phone calls and allows the user to send voice commands to the control unit 16. The microphone 22 is electronically connected to the controller 17. This arrangement allows audio captured by the microphone 22 to be subsequently interpreted by the controller 17.

Although the invention has been explained in relation to its preferred embodiment, it is to be understood that many other possible modifications and variations can be made without departing from the spirit and scope of the invention as hereinafter claimed.

What is claimed is:

1. A wireless stereo sleep mask comprising:
an eye cover;
an elastic strap;
a first speaker;
a second speaker;
a control unit;
a wireless transceiver;
a casing;
the eye cover comprising an enclosure, a padding, a first temple-bracing portion and a second temple-bracing portion;
the padding being positioned within the enclosure;
the padding being distributed throughout the enclosure;
the first temple-bracing portion and the second temple-bracing portion each being formed on the enclosure;
the first temple-bracing portion and the second temple-bracing portion being oppositely positioned to each other across the enclosure;
the elastic strap comprising a sleeve, an elastic mesh band, a first pocket, a second pocket and an access opening;
the elastic mesh band traversing through the sleeve;
the sleeve comprising a first sleeve end and a second sleeve end;
the first sleeve end and the second sleeve end being oppositely positioned to each other across the sleeve;
the first pocket traversing into the first sleeve end;
the first pocket being telescopically engaged into the first sleeve end;
the second pocket traversing into the second sleeve end;
the second pocket being telescopically engaged into the second sleeve end;
the elastic mesh band comprising a first band end and a second band end;
the first band end and the second band end being oppositely positioned to each other across the elastic mesh band;
the first band end traversing into the first pocket;
the second band end traversing into the second pocket;
the first band end being connected with the first pocket;
the second band end being connected with the second pocket;
the first temple-bracing portion being terminally connected to the first pocket;
the second temple-bracing portion being terminally connected to the second pocket;
the first speaker being situated within the first pocket;
the second speaker being situated within the second pocket;
the first speaker being adjacently positioned to the first temple-bracing portion;
the second speaker being adjacently positioned to the second temple-bracing portion;
the wireless transceiver being electronically connected to the control unit; and
the control unit being electrically connected to the first speaker and the second speaker;
the wireless transceiver and the control unit being housed within the casing;
the access opening being formed in between the sleeve and the first pocket or in between the sleeve and the second pocket; and
the casing being capable of being situated within the sleeve or the first pocket or the second pocket through the access opening.

2. The wireless stereo sleep mask as claimed in claim 1 comprising:
the enclosure is a velvety enclosure.

3. The wireless stereo sleep mask as claimed in claim 1 comprising:
a length of the sleeve being greater than a length of the elastic mesh band.

4. The wireless stereo sleep mask as claimed in claim 1 comprising:
the first speaker and the second speaker each being tethered to the casing.

5. The wireless stereo sleep mask as claimed in claim 1 comprising:
the control unit comprising a controller, a charging port and a portable power source;
the portable power source being electrically connected to the charging port and the controller; and
the first speaker, the second speaker and the wireless transceiver being electronically connected to the controller.

6. The wireless stereo sleep mask as claimed in claim 5 comprising:
the control unit comprising a volume adjustment module; and
the volume adjustment module being electronically connected to the controller.

7. The wireless stereo sleep mask as claimed in claim 5 comprising:
the control unit comprising a user interface; and
the user interface being electronically connected to the controller.

8. The wireless stereo sleep mask as claimed in claim 5 comprising:
the control unit comprising a microphone; and the microphone being electronically connected to the controller.

\* \* \* \* \*